US008545429B2

(12) United States Patent
Batzdorf

(10) Patent No.: US 8,545,429 B2
(45) Date of Patent: Oct. 1, 2013

(54) SYRINX CAVITY SHUNT DEVICE AND METHOD

(76) Inventor: Ulrich Batzdorf, Santa Monica, CA (US)

( * ) Notice: Subject to any disclaimer, the term of this patent is extended or adjusted under 35 U.S.C. 154(b) by 675 days.

(21) Appl. No.: 12/725,176

(22) Filed: Mar. 16, 2010

(65) Prior Publication Data

US 2011/0230815 A1      Sep. 22, 2011

Related U.S. Application Data

(60) Provisional application No. 61/215,639, filed on May 7, 2009.

(51) Int. Cl.
*A61M 5/00*        (2006.01)
(52) U.S. Cl.
USPC .................................. 604/8; 604/9
(58) Field of Classification Search
USPC ............... 604/8–10, 175, 247, 280, 264, 268, 604/523, 530, 540–544
See application file for complete search history.

(56) References Cited

U.S. PATENT DOCUMENTS

| | | | | |
|---|---|---|---|---|
| 4,531,933 A | * | 7/1985 | Norton et al. | 604/8 |
| 5,405,316 A | * | 4/1995 | Magram | 604/8 |

OTHER PUBLICATIONS

Youmans, "Neurological Surgery", Fourth Edition, vol. 2, 1996.
Schmidek et al., "Operative Neurosurgical Techniques: Indications, Methods, and Results", vol. 2, Fifth Edition, 2006.
Batzdorf et al., "Chiari Malformation and Syringomyelia—A Handbook for Patients and their Families", 2008.
Barbaro et al., "Surgical Treatment of Syringomyelia—Favorable Results with Syringoperitoneal Shunting", J. Neurosurg., vol. 61, Sep. 1984.
Ventureyra et al., "Syringostomy Using Myringostomy Tube: Technical Note", Neurosurgery, vol. 41, No. 2, Aug. 1997.
Sgouros et al., "A Critical Appraisal of Drainage in Syringomyelia", J. Neurosurg., vol. 82, Jan. 1995.
Batzdorf et al., "A Critical Appraisal of Syrinx Cavity Shunting Procedures", J. Neurosurg., vol. 89, Sep. 1998.
Wester et al., "Spinal Cord Damage Caused by Rotation of a T-Drain in a Patient with Syringoperitoneal Shunt", Surg. Neurol., 1989.

* cited by examiner

*Primary Examiner* — Philip R Wiest

(57) ABSTRACT

A shunt is provided having a first catheter end with one or more apertures that provide access to an interior of the shunt. At least a portion of the first catheter end has a substantially helical shape and the one or more apertures are disposed on an interior surface of the substantially helical shape of the first catheter end. The shunt also includes a second catheter end providing access to the interior of the shunt for drainage of the shunt at a remote location. The shunt further includes a catheter body disposed between the first catheter end and the second catheter end.

20 Claims, 2 Drawing Sheets

SYRINX CAVITY SHUNT DEVICE AND METHOD

PRIORITY

This application claims priority under 35 U.S.C. §119(e) to a provisional application filed in the U.S. Patent and Trademark Office on May 7, 2009 and assigned Ser. No. 61/215,639, the contents of which are incorporated herein by reference.

BACKGROUND OF THE INVENTION

1. Field of the Invention

The present invention relates generally to shunts, and more particularly to shunts for syrinx cavity drainage and associated procedures, including percutaneous introduction and deployment.

2. Description of Related Art

Syringomyelia is a condition in which a cyst forms within the spinal cord, and is filled with fluid essentially identical with CerebroSpinal Fluid (CSF). Syringomyelic cavities are generally thought to develop when there is a partial obstruction to the circulation of CSF within the subarachnoid space, thereby causing migration of fluid through the substance of the spinal cord for collection within the spinal cord. Dynamic relationships of CSF pulsatiltity and physiological transient pressure changes cause the fluid cavity within the cord to become distended and to expand in an upward and/or downward direction, thereby destroying spinal cord tissue and impairing spinal cord function, resulting in permanent damage. In extreme situations, the damage may take the form of paraplegia or quadriplegia. Other symptoms include pain, numbness, weakness, disruption in temperature sensation, adverse effects on sweating, sexual function, and bladder and bowel control.

The referenced (partial) obstruction may derive from an abnormality of the brain called an Arnold-Chiari malformation, where the lower part of the cerebellum protrudes from its normal location at the back of the head into the cervical portion of the spinal canal. Syringomyelia may also occur as a result of complications from trauma, meningitis, hemorrhaging, a tumor, or arachnoiditis.

As reported in Batzdorf, et al., "A Clinical Appraisal of Syrinx Cavity Shunting Procedures," J Neurosurg 89:382-388, 1998, Chiari-related syringomyelia is generally considered to be best treated by eliminating the partial block by suboccipital decompression. Likewise, spinal decompression and arachnoid scar resection, with placement of a dural graft is recommended in appropriate cases of primary spinal syringomyelia when the obstruction to CSF flow is very limited to a narrow area. In any case, the primary goal is one of reestablishing unrestricted subarachnoid CSF flow.

Some conditions, however, do not lend themselves to the treatment approaches referred to above. For example, in many instances of syringomyelia that develop after spinal cord injury, the scar tissue surrounding the spinal cord is not limited to a narrow, more easily treatable band, but instead extends circumferentially around the cord and over several vertebral segments. Problematic diffuse arachnoid scarring is also seen after meningitis and in some patients following subarachnoid hemorrhage. In these cases, shunt placement presents a viable treatment option, and is often the only available treatment.

It is to be appreciated that existing shunt devices used in humans present an approximately 50% failure rate. Batzdorf, et al. further reports on several failure modes for existing devices. Shunt obstruction is the most common of these failure modes. In existing devices that provide drainage through a port, or ports, only at the tip of the device, collapse of the syrinx cavity can terminate proper function. In other devices in which lateral drainage holes are provided, tissue in-growth has also been observed. In-growth of glial tissue may make it impossible to withdraw a shunt tube during attempted revision, thereby resulting in further complications. In a T-shaped device, with one arm directed upward into the cavity, and the other arm downward, in-situ rotation of the device risked spinal cord injury.

After some considerable time since reporting the failure modes, no adequate alternative has yet been made available to physicians to treat the patient population in need.

SUMMARY OF THE INVENTION

The present invention has been made to address at least the above problems and/or disadvantages and to provide at least the advantages described below. Accordingly, an aspect of the present invention provides a shunt and a method of administration of the shunt for effective drainage.

According to one aspect of the present invention, a shunt is provided having a first catheter end with one or more apertures that provide access to an interior of the shunt. At least a portion of the first catheter end has a substantially helical shape and the one or more apertures are disposed on an interior surface of the substantially helical shape of the first catheter end. The shunt also includes a second catheter end providing access to the interior of the shunt for drainage of the shunt at a remote location. The shunt further includes a catheter body disposed between the first catheter end and the second catheter end.

According to another aspect of the present invention, a method of administering a shunt is provided. A first catheter end of the shunt is introduced into a cavity. An obturator is disposed within an interior of the first catheter end to prevent flow through the shunt and to maintain a straightened shape of the first catheter end. Removing the obturator from the first catheter end enables at least a portion of the first catheter end to assume a substantially helical shape within the cavity. A second catheter end of the shunt is introduced to a remote location for drainage of fluid from an interior of the shunt.

According to a further aspect of the present invention, a shunt is provided having a first catheter end with at least one aperture that provides access to an interior of the shunt. At least a portion of the first catheter end has a substantially helical shape and the at least one aperture is within an area defined by an interior of the substantially helical shape of the first catheter end. The shunt also includes a second catheter end having access to the interior of the shunt for drainage of the shunt at a remote location. The shunt further includes a catheter body disposed between the first catheter end and the second catheter end.

BRIEF DESCRIPTIONS OF THE DRAWINGS

The above and other aspects, features and advantages of the present invention will be more apparent from the following description when taken in conjunction with the accompanying drawings, in which.

DETAILED DESCRIPTION OF EMBODIMENTS OF THE PRESENT INVENTION

Figure 1:
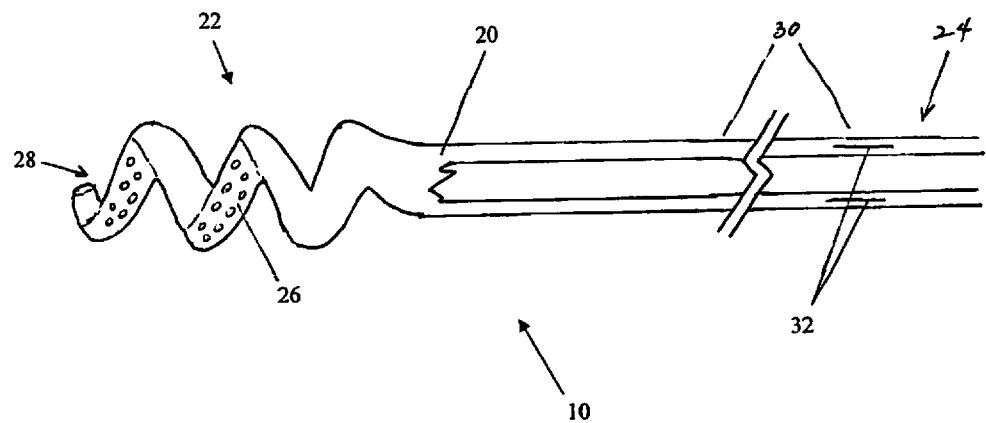
FIG. 1 is a diagram illustrating a shunt, according to a first embodiment of the present invention.

Embodiments of the present invention are described in detail with reference to the accompanying drawings. The same or similar components may be designated by the same or similar reference numerals although they are illustrated in different drawings. Detailed descriptions of constructions or processes known in the art may be omitted to avoid obscuring the subject matter of the present invention.

The terms and words used in the following description and claims are not limited to their dictionary meanings, but are merely used to enable a clear and consistent understanding of the invention. Accordingly, it should be apparent to those skilled in the art that the following description of embodiments of the present invention are provided for illustrative purposes only and not for the purpose of limiting the invention, as defined by the appended claims and their equivalents.

It is to be understood that the singular forms "a," "an," and "the" include plural referents unless the context clearly dictates otherwise. Thus, for example, reference to "an identifier" includes reference to one or more of such identifiers.

Referring initially to FIG. 1, a diagram illustrates a shunt, according to a first embodiment of the present invention. A shunt 10 includes a catheter body 20 with a first end 22 having a spiral/helical shape for placement within a spinal cord cyst (syringomyelic cavity), and a second end 24 for drainage at a selected site. Ports/apertures 26 are provided along an interior surface of the helical shape, and are in communication with a collection zone 28 defined by the deployed shape of the catheter tube. The helical shape may also serve as a shield to define the collection zone 28 and may include transverse channels for passing fluid to the ports 26. FIG. 1 illustrates a simple helical shape having an end that may be left open. Alternative embodiments may include a two-start helix having an end that provides a continuous transition between separate arms.

The protected interior drainage ports 26 avoid shunt problems described above, as well as others that may be apparent to those skilled in the art. The position of the ports 26 within the collection zone 28 avoids tissue in-growth interference. Additionally, the helical shape protects the shunt from collapse.

The ports 26 may be set between about 1 and about 3 mm apart. Depending on their number and arrangement, the ports 26 may have a size between about 0.5 and about 1.5 mm, or more preferably between about 0.75 and about 1 mm. The ports 26 may be staggered and provided in multiple sets as shown in FIG. 1. The ports 26 may also be arranged in a simple linear fashion, or configured in another manner.

As shown in FIG. 1, an extension section 30 of the shunt 10 has a length set for positioning the second end 24 at a remote location. The second end 24 optionally includes one or more valves, such as simple slit-type valves 32. Remote locations include, but are not limited to, the spinal subarachnoid space beyond the area of an abnormality, the peritoneal cavity or the pleural cavity. As with a conventional shunt, the catheter body may include a fixation tab (not shown) to anchor its location using a suture.

To introduce the shunt, a subcutaneous tunneling device, such as the Subcutaneous Catheter Passer, by HDC Corp., may be employed to develop a passageway for the subject device. Such a device may comprise a tubular steel shaft with a T-handle, along with a bullet-shaped tip obturator. Often, the end of the shunt to be placed within the syrinx cavity is introduced under direct vision using a surgical microscope. The tunnel to peritoneal or pleural cavity can be facilitated utilizing the Catheter Passer.

Figures 2A, 2B, 2C:
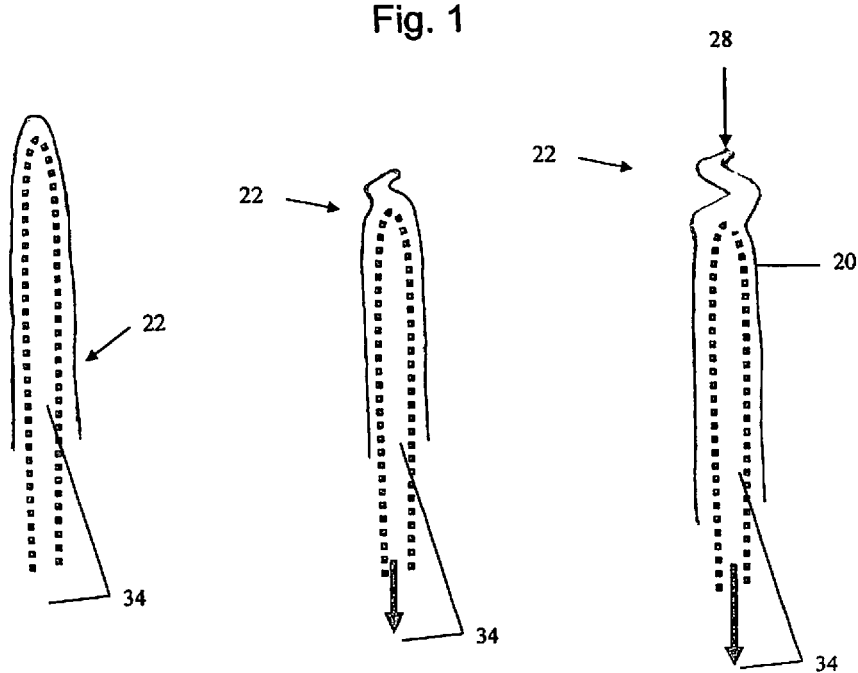
FIGS. 2A-2C are diagrams illustrating deployment of a shunt, according to a second embodiment of the present invention.
Figure 3:
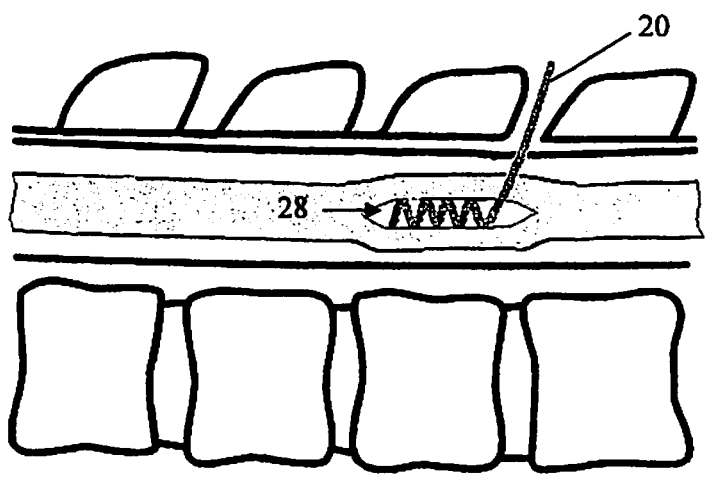
FIG. 3 is a diagram illustrating a shunt suitably positioned to drain a syrinx cavity, according to an embodiment of the present invention.
Figure 4:
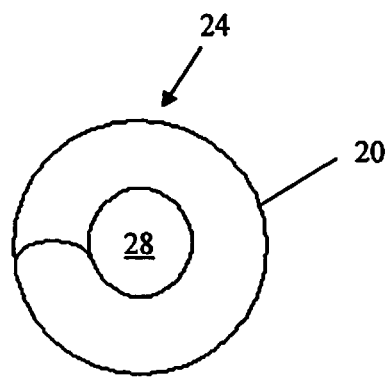
FIG. 4 is a diagram illustrating an end view of a shunt, according to an embodiment of the present invention.

At the treatment site, an obturator/stiffening element 34 is pulled from the device allowing a relatively straightened distal section, as shown in FIG. 2A, to progressively resume its biased helical shape, as shown in FIGS. 2B and 2C. A single-lumen device is shown, however, the same methodology can be employed for a dual helical device. FIG. 3 illustrates a shunt suitably positioned to drain a syrinx cavity, according to an embodiment of the present invention. An end view of the drainage cistern or collection zone 28 is illustrated in FIG. 4, according to an embodiment of the present invention.

In instances where tissue in-growth interference occurs, the spiral shape allows the device to backed-out by twisting, as if the shunt was being unscrewed. Such a removal possibility maintains the potential for retreatment without having to cut off and leave an ingrown shunt in place.

In every variation of the subject invention, the pitch of the spiral may vary along its length, or it may be constant. However configured, the spiral/helical portion of the shunt typically has a has a distal diameter that is generally between about 2 and about 4 mm, with an internal collection zone defined by successive coils of at least about 1 mm in diameter, and more preferably between about 1 mm and 2 mm. However, various dimensional changes and/or optimization for syrinx cavity drainage or use in other applications may be undertaken without departing from the intended scope of the present invention.

A number of materials and constructions employed in catheter technology may be used for producing a resilient structure capable of transforming between a straightened and a coiled shape. In one such approach, a tubular braid set in a helical/coil shape is embedded within the shunt wall. In another approach, a wound spring coil is set in a secondary helical/coil shape and clad with polymer.

The polymer forming the wall or shell of the catheter, especially in the helical region, may include silicone, specifically, barium- or tantalum-loaded silicone. The polymer may also include one or more radiopaque marker bands to assist in visualization. Alternatively, visualization during implantation may be accomplished via the obturator when in place, and by contrast injection during and after obturator removal. The obturator may be configured to allow contrast injection/perfusion there through, or it may be grooved to allow its passage.

Laser ablation techniques may be employed to form the ports or apertures in the helical construct. Other punch-type techniques may be employed as well as other drainage catheter construction techniques known by those skilled in the art.

While the invention has been shown and described with reference to certain embodiments thereof, it will be understood by those skilled in the art that various changes in form and detail may be made therein without departing from the spirit and scope of the invention as defined by the appended claims and their equivalents.

What is claimed is:

1. A shunt comprising:
   a first catheter end having a plurality of apertures that provide access to an interior of the shunt, wherein at least a portion of the first catheter end has a substantially helical shape with an interior surface that defines a collection area, the plurality of apertures are disposed on the interior surface of the substantially helical shape in communication with the collection area, and access to the interior of the shunt at the first catheter end is only provided through the plurality of apertures;

a second catheter end providing access to the interior of the shunt for drainage of the shunt at a remote location; and a catheter body disposed between the first catheter end and the second catheter end.

2. The shunt of claim 1, wherein the collection area is disposed within at least one of a spinal cord cyst and a syringomyelic cavity.

3. The shunt of claim 1, wherein the remote location comprises one of a spinal subarachnoid space, a peritoneal cavity, and a pleural cavity.

4. The shunt of claim 1, wherein the plurality of apertures comprises staggered apertures that are disposed in a plurality of sets.

5. The shunt of claim 1, further comprising a valve for providing access to the interior of the shunt.

6. The shunt of claim 1, wherein a length of the catheter body is determined in accordance with a placement of the first catheter end and a placement of the second catheter end.

7. The shunt of claim 1, wherein placement of the plurality of apertures on the interior of the substantially helical shape of the first catheter end protects the plurality of apertures from occlusion due to tissue in-growth.

8. The shunt of claim 1, wherein the substantially helical shape of the first catheter end protects the first catheter end from collapse.

9. The shunt of claim 1, wherein the substantially helical shape allows for removal of the first catheter end via an unscrewing motion.

10. The shunt of claim 1, wherein placement of the plurality of apertures on the interior of the substantially helical shape of the first catheter end protects the first catheter end from collapse.

11. The shunt of claim 1, wherein the first catheter end comprises a two-start helix.

12. A method of administering a shunt comprising the steps of:

introducing a first catheter end of the shunt into a cavity, wherein an obturator is disposed within an interior of the first catheter end to prevent flow through the shunt and to maintain a straightened shape of the first catheter end;

removing the obturator from the first catheter end enabling at least a portion of the first catheter end to assume a substantially helical shape within the cavity, wherein the substantially helical shape has an interior surface that defines a collection area, a plurality of apertures are disposed on the interior surface of the substantially helical shape in communication with the collection area, and access to the interior of the shunt at the first catheter end is only provided through the plurality of apertures; and introducing a second catheter end of the shunt to a remote location for drainage of fluid from an interior of the shunt.

13. The method of claim 12, wherein the one or more apertures enable introduction of flow from the first catheter end to the second catheter end.

14. The method of claim 13, wherein the collection area is disposed within at least one of a spinal cord cyst and a syringomyelic cavity.

15. The method of claim 12, wherein the remote location comprises one of a spinal subarachnoid space, a peritoneal cavity, and a pleural cavity.

16. The method of claim 12, wherein the plurality of apertures comprises staggered apertures that are disposed in a plurality of sets.

17. The method of claim 12, wherein placement of the plurality of apertures on the interior of the substantially helical shape of the first catheter end protects the plurality of apertures from occlusion due to tissue in growth and protects the first catheter end from collapse.

18. The method of claim 12, wherein the first catheter end comprises a two-start helix.

19. A shunt comprising:

a first catheter end having a plurality of apertures that provide access to an interior of the shunt, wherein at least a portion of the first catheter end has a substantially helical shape, the plurality of apertures are within an area defined by an interior of the substantially helical shape of the first catheter end, and access to the interior of the shunt at the first catheter end is only provided through the plurality of apertures;

a second catheter end having access to the interior of the shunt for drainage of the shunt at a remote location; and a catheter body disposed between the first catheter end and the second catheter end.

20. The shunt of claim 19, wherein the first catheter end comprises a two-start helix.

* * * * *